US00PP08876P

United States Patent [19]

Stravers

[11] Patent Number: Plant 8,876

[45] Date of Patent: Aug. 30, 1994

[54] *GERBERA JAMESONII* PLANT NAMED TERTONO

[75] Inventor: Lambertus J. M. Stravers, Carlsbad, Calif.

[73] Assignee: Terra Nigra B.V., De Kwakel, Netherlands

[21] Appl. No.: 172,262

[22] Filed: Dec. 23, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

[57] ABSTRACT

A new and distinct cultivar of Gerbera plant named 'Tertono' as illustrated and described, characterized by its semi-double type, a very distinct dark pink ray floret with white edges, a green disc floret, the outermost florets of which display white stigmas and the middle flowers of which show yellow anthers, pink perianth lobe color and 110 mm overall flower diameter.

1 Drawing Sheet

BACKGROUND OF THE INVENTION

The present invention comprises a new and distinct cultivar of *Gerbera jamesonii*, referred to by the cultivar name 'Tertono'. 'Tertono' was originated from a hybridization program in De Kwakel, The Netherlands in 1989. The female parent was '83.740', and the male parent was '86.303'. The female parent '83.740' differs from 'Tertono' by its orange color, its very high productivity, and its good vase-life. '83.740' has not been patented in the United States. It has been available to others outside the company. The male parent '86.303' differs from 'Tertono' by its different pink color (more lilac), its reasonable productivity, and its smaller diameter. '86.303' has not been patented in the United States. It was not available to others outside the company. The new cultivar was selected by me from the progeny of the stated parentage on or about November 1989. The first asexual reproduction of 'Tertono' was accomplished when vegetative cuttings for tissue culture initiation were taken on November 1989 in De Kwakel, The Netherlands. The new cultivar is presently being propagated by cuttings and tissue culture. Horticultural examination of selected units initiated November 1989 has demonstrated that the combination of characteristics as herein disclosed for 'Tertono' are firmly fixed and are retained through successive generations of asexual reproduction.

The following observations, measurements and comparisons describe plants grown in De Kwakel, The Netherlands, under greenhouse conditions which closely approximate those generally used in commercial practice. The following traits have been repeatedly observed and are determined to be basic characteristics of 'Tertono', which in combination distinguish this Gerbera from its parents and all other varieties of which I am aware:

1. Type: Semi-double
2. Color of ray floret: Distinctive dark pink
3. Color of disc floret: Green
4. Color of perianthy lobe: Pink
5. Diameter of flower head: Large (approx. 110 mm)

Of the many commercial cultivars known to me, there is no cultivar similar in comparison to 'Tertono'.

BRIEF DESCRIPTION OF THE FIGURE OF THE DRAWING

The accompanying photographic drawing shows typical inflorescence characteristics nearly true as possible. In the following description, color references are made to The Royal Horticultural Society Color Chart (RHS). The color values were determined at approximately 14:15 p.m. on Sep. 11, 1993 under natural light at De Kwakel.

BOTANICAL DESCRIPTION OF THE PLANT

Botanical: *Gerbera jamesonii* cv. Tertono.

INFLORESCENCE

A. Capitulum:
- *Form.*—Flat-shaped.
- *Type.*—Semi-double.
- *Diameter across face.*—110 mm.

B. Corolla of ray florets:
- *Color (general tonality from a distance of 3 meters)*.—Dark pink.
- *Color (topside).*—Pink (RHS 50A).
- *Color (bottom).*—Yellow (RHS 38C).

C. Corolla of disc florets:
- *Color (mature).*—Green (RHS 153B).
- *Color (immature).*—Green (RHS 153B).

D. Reproductive organs:
- *Stigma.*—White (RHS 155C).
- *Anthers.*—Yellow (RHS 15B).
- *Pappus.*—Yellow (RHS 10D).

PLANT

A. General appearance:
- *Height.*—40 cm.

B. Foliage:
- *Color (abaxial).*—Green RHS 139A.
- *Color (adaxial).*—Green RHS 139A.
- *Shape.*—The angle of apex: Right angle. The shape of apex: Rounded. The margin of lobes: Crenate.

C. Disease resistance: No special disease resistance.

OTHER CHARACTERISTICS

The following traits have been repeatedly observed and are determined to be basic characteristics of 'Tertono', which in combination distinguish this Gerbera as a new and distinct cultivar.

Leaf blade:
*Length.*—Medium.
*Width.*—Medium.
*Thickness.*—Medium.
*Blistering.*—Medium.
*Pubescence.*—On upper side (midrib excluded): Medium.
*Depth of cuts or incisions in leaf.*—Basal part: Deep. Central part: Deep. Distal part: Shallow.
*Color.*—Upper side of the leaf blade is green (RHS 139A).
*Glossiness on upper side.*—Medium.
*Angle of apex.*—Right angle.
*Shape of apex.*—Rounded.
*Margin of lobes.*—Crenate.
*Extensions of margin.*—Medium.
*Petiole length.*—Long; approx. 12 cm.
*Petiole anthocyanin coloration.*—Strong.

Peduncle:
*Length.*—Medium (approx. 60 cm).
*Cross section.*—Round.
*Tendency to fasciation.*—Absent.
*Thickness.*—Medium.
*Strength.*—Medium.
*Pubescence.*—Medium.
*Color.*—Medium green.
*Anthocyanin coloration.*—At base: Strong. At top: Absent.
*Involucral bracts.*—Present.

Flower head:
*Type.*—Semi-double.
*Diameter.*—Large (approx. 110 mm).
*Involucre.*—Height: Medium (20 mm). Diameter: Medium (45 mm). Number of bracts: Medium (approx. 67). Longitudinal axis of bracts of inner rows: Straight. Anthocyanin: Absent. Pubescence: Medium.
*Ray florets.*—Number: Medium (approx. 68). Shape: Obovate. Longitudinal axis outer row: Reflexing. Longitudinal axis inner row: Straight.
*Outer ray florets.*—Cross section: Flat. Length: Medium (50 mm). Width: Medium. Longitudinal folding: Medium. Angle of apex: Right angle. Shape of apex: Rounded. Incisions of apex: Present. Number: one or two. Depth: medium. Length of free petals: very long. Color distribution on inner side: Uniform. Edge of different color: Edge is white. Striation: Absent. Claw spot: Present.

Disc florets:
*Diameter.*—Medium (approx. 45 mm).
*Main color perianth lobes.*—Female flowers: pink (RHS 52A). Male flowers: pink (RHS 52C).

Reproductive parts:
*Stigma.*—Main color white (RHS 155C).
*Anthers.*—Main color yellow (RHS 15B).
*Pappus.*—Main color yellow (RHS 10D).
*Fertility.*—Fertility as well as the seedsetting are good.

I claim:

1. A new and distinct cultivar of Gerbera plant named 'Tertono' as illustrated and described, characterized by its semi-double type, a very distinct dark pink ray floret with white edges, a green disc floret, the outermost florets of which display white stigmas and the middle flowers of which show yellow anthers, pink perianth lobe color and 110 mm overall flower diameter.

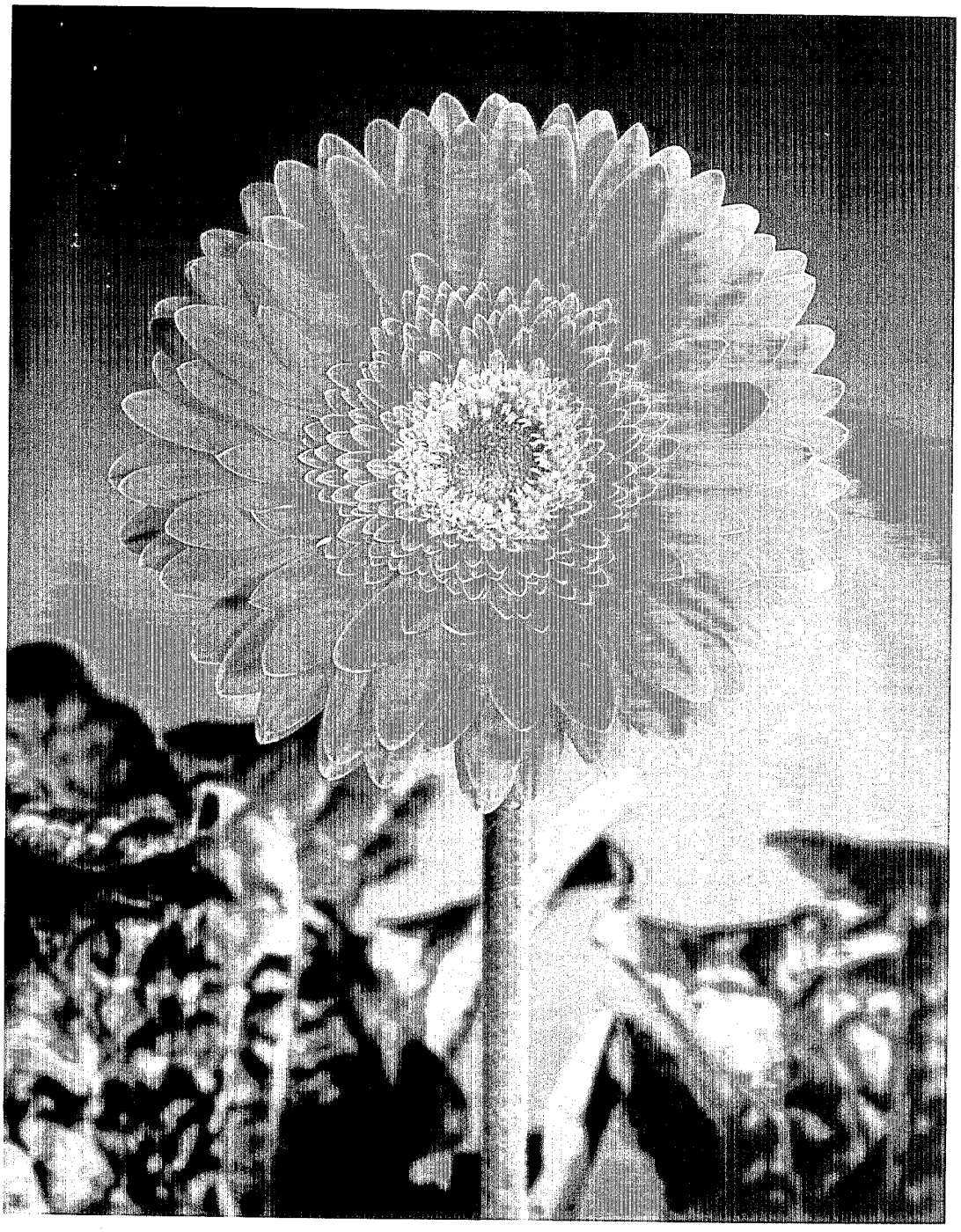

* * * * *